US012599411B2

(12) United States Patent
Oikawa et al.

(10) Patent No.: US 12,599,411 B2
(45) Date of Patent: Apr. 14, 2026

(54) ROD FOR SPINAL BRACE

(71) Applicant: GLOBERIDE, Inc., Tokyo (JP)

(72) Inventors: Katsuhiro Oikawa, Tokyo (JP); Takuji Kawamura, Tokyo (JP)

(73) Assignee: GLOBERIDE, INC., Tokyo (JP)

( * ) Notice: Subject to any disclaimer, the term of this patent is extended or adjusted under 35 U.S.C. 154(b) by 201 days.

(21) Appl. No.: 18/027,818

(22) PCT Filed: Sep. 10, 2021

(86) PCT No.: PCT/JP2021/033268
§ 371 (c)(1),
(2) Date: Mar. 22, 2023

(87) PCT Pub. No.: WO2022/070834
PCT Pub. Date: Apr. 7, 2022

(65) Prior Publication Data
US 2023/0329756 A1     Oct. 19, 2023

(30) Foreign Application Priority Data
Sep. 29, 2020     (JP) ................................. 2020-163964

(51) Int. Cl.
*A61B 17/70*        (2006.01)
*A61L 31/12*        (2006.01)
(52) U.S. Cl.
CPC ........ *A61B 17/7002* (2013.01); *A61L 31/128* (2013.01)

(58) Field of Classification Search
CPC ........ A61B 17/7002–17/7013; A61B 17/7019; A61B 17/7026; A61B 17/7029–17/7031
See application file for complete search history.

(56) References Cited

U.S. PATENT DOCUMENTS

| | | | |
|---|---|---|---|
| 5,415,661 A | 5/1995 | Holmes | |
| 5,556,687 A * | 9/1996 | McMillin | ........... A61B 17/7007 |
| | | | 87/8 |
| 2004/0049189 A1 | 3/2004 | Le Couedic et al. | |
| 2004/0215191 A1 | 10/2004 | Kitchen | |
| 2006/0189982 A1* | 8/2006 | Lange | .................. A61B 17/701 |
| | | | 606/301 |
| 2006/0247638 A1 | 11/2006 | Trieu et al. | |

(Continued)

FOREIGN PATENT DOCUMENTS

| | | |
|---|---|---|
| DE | 102013013024 A1 | 2/2014 |
| EP | 2389124 | 11/2011 |

(Continued)

OTHER PUBLICATIONS

International Search Report for related International Application No. PCT/JP2021/033268; action dated Apr. 7, 2022; (5 pages).

(Continued)

*Primary Examiner* — Julianna N Harvey
(74) *Attorney, Agent, or Firm* — Oliff PLC

(57) ABSTRACT
A fixture rod which reduces damage at the time of fixing with a screw, has high rigidity, and has high durability against a deformation load is provided. A fixture rod according to one embodiment of the present disclosure is configured to comprise a core member and a reinforcing fiber layer provided on the core member.

8 Claims, 5 Drawing Sheets

(56) References Cited

U.S. PATENT DOCUMENTS

| | | | |
|---|---|---|---|
| 2006/0276788 A1 | 12/2006 | Berry et al. | |
| 2007/0233073 A1 | 10/2007 | Wisnewski et al. | |
| 2008/0177317 A1 | 7/2008 | Jackson | |
| 2008/0234744 A1 | 9/2008 | Zylber et al. | |
| 2008/0262548 A1 | 10/2008 | Lange et al. | |
| 2009/0018583 A1 | 1/2009 | Song et al. | |
| 2009/0093819 A1* | 4/2009 | Joshi | A61B 17/7004 |
| | | | 606/103 |
| 2009/0112265 A1 | 4/2009 | Hudgins et al. | |
| 2009/0118831 A1* | 5/2009 | Trieu | A61B 17/7035 |
| | | | 606/279 |
| 2009/0163955 A1* | 6/2009 | Moumene | A61B 17/701 |
| | | | 606/257 |
| 2009/0281573 A1 | 11/2009 | Biedermann et al. | |
| 2009/0287251 A1 | 11/2009 | Bae et al. | |
| 2010/0137912 A1 | 6/2010 | Alcock et al. | |
| 2011/0060365 A1 | 3/2011 | Felix et al. | |
| 2011/0071570 A1 | 3/2011 | Trieu | |
| 2011/0106162 A1* | 5/2011 | Ballard | A61B 17/701 |
| | | | 606/279 |
| 2011/0152937 A1 | 6/2011 | Trieu | |
| 2011/0282395 A1 | 11/2011 | Beyar et al. | |
| 2011/0307014 A1 | 12/2011 | Niinomi et al. | |
| 2012/0029564 A1* | 2/2012 | Trieu | A61B 17/7029 |
| | | | 29/447 |
| 2012/0071928 A1 | 3/2012 | Jackson | |
| 2012/0196068 A1 | 8/2012 | Gong et al. | |
| 2013/0204368 A1 | 8/2013 | Prevost | |
| 2013/0213535 A1 | 8/2013 | Niinomi et al. | |
| 2015/0209095 A1 | 7/2015 | Lu et al. | |
| 2016/0303824 A1 | 10/2016 | Takebe et al. | |
| 2017/0042593 A1* | 2/2017 | Newman | A61L 31/126 |
| 2017/0304073 A1 | 10/2017 | Pedoulias et al. | |
| 2024/0058038 A1 | 2/2024 | Oikawa et al. | |

FOREIGN PATENT DOCUMENTS

| | | | |
|---|---|---|---|
| EP | 2 982 504 A1 | 2/2016 | |
| EP | 3236866 | 11/2017 | |
| GB | 2256615 A | 12/1992 | |
| JP | H04-366616 A | 12/1992 | |
| JP | H11-296033 A | 10/1999 | |
| JP | H11-347047 A | 12/1999 | |
| JP | 2011-508623 A | 3/2011 | |
| JP | 2011-256443 A | 12/2011 | |
| JP | 2015186641 A | 10/2015 | |
| JP | 2020137454 A | 9/2020 | |
| KR | 102187523 B1 | 12/2020 | |
| WO | 2006/044315 A2 | 4/2006 | |
| WO | 2007/097905 A2 | 8/2007 | |
| WO | 2011/042998 A1 | 4/2011 | |
| WO | 2014/162873 A1 | 10/2014 | |

OTHER PUBLICATIONS

Written Opinion for related International Application No. PCT/JP2021/033268; action dated Apr. 7, 2022; (4 pages).

Dec. 11, 2024 Office Action issued in Chinese Patent Application No. 202180053600.2.

Nov. 21, 2023 Office Action issued in Japanese Patent Application No. 2020-163964.

Office Action for related Japanese Application No. 2020-163964; action dated Jun. 27, 2023; (7 pages).

Apr. 26, 2024 Search Report issued in European Patent Application No. 21875136.0.

Preliminary Report on Patentability for related International Application No. PCT/JP2021/033268; action dated Mar. 28, 2023; (9 pages).

Feb. 19, 2025 Office Action issued in Korean Patent Application No. 10-2023-7006589.

Jun. 19, 2025 Office Action issued in Chinese Patent Application No. 202180053600.2.

Sep. 27, 2025 Office Action issued in Chinese Patent Application No. 202180088813.9.

Aug. 11, 2025 Office Action issued in U.S. Appl. No. 18/269,488.

Jul. 15, 2025 Office Action issued in Korean Patent Application No. 10-2023-7028508.

Dec. 5, 2023 Office Action issued in Japanese Patent Application No. 2021-000613.

Jul. 2, 2024 Extended European Search Report issued in European Patent Application No. 21917551.0.

Mar. 31, 2025 Office Action issued in U.S. Appl. No. 18/269,488.

Jul. 4, 2023 International Preliminary Report issued in International Patent Application No. PCT/JP2021/037720.

Jul. 14, 2022 International Search Report issued in International Patent Application No. PCT/JP2021/037720.

Jul. 14, 2022 Written Opinion issued in International Patent Application No. PCT/JP2021/037720.

May 20, 2025 Office Action issued in Korean Patent Application No. 10-2023-7023502.

Jul. 31, 2024 Extended European Search Report issued in European Patent Application No. 21921161.2.

Dec. 5, 2023 Office Action issued in Japanese Patent Application No. 2021-009692.

International Preliminary Report on Patentability for related International Application No. PCT/JP2021/037721; action dated Jul. 20, 2023; (12 pages).

International Search Report for related International Application No. PCT/JP2021/037721; action dated Jul. 28, 2022; 3 pages).

Written Opinion for related International Application No. PCT/JP2021/037721; action dated Jul. 28, 2022; (5 pages).

Aug. 11, 2025 Office Action issued in U.S. Appl. No. 18/272,981.

Apr. 11, 2025 Office Action issued in U.S. Appl. No. 18/272,981.

18/272, 981 Feb. 5, 2026 Office Action issued in U.S. Appl. No. 18/727,981.

Jan. 15, 2026 Office Action issued in U.S. Appl. No. 18/269,488.

Dec. 25, 2025 Office Action issued in Chinese Patent Application No. 202180091658.6.

Feb. 7, 2026 Office Action issued in Chinese Patent Application No. 202180088813.9.

* cited by examiner

ROD FOR SPINAL BRACE

CROSS-REFERENCE TO RELATED APPLICATIONS

The present application is a National Stage of International Application No. PCT/JP2021/033268 filed on Sep. 10, 2021 which claims priority to and the benefit of Japanese Patent Application No. 2020-163964 filed on Sep. 29, 2020, the contents of which are incorporated herein by reference in their entirety.

FIELD

The present disclosure relates to a fixture rod used for a fixture for fixing the spine.

BACKGROUND

Conventionally, a fixture rod using metal as a fixture for fixing the spine has been known.

Further, as such a fixture rod, for example, Patent Literature 1 discloses a spinal pedicle rod including an internally reinforced polymer core at least partially encased in a polymer coating.

CITATION LIST

Patent Literature

Patent Literature 1: Japanese Translation of PCT International Application Publication No. 2011-508623.

SUMMARY

A fixture rod using metal is generally excellent in fixing force and strength, but has a problem that a magnetic field is affected by magnetization of the metal in the magnetic field at the time of imaging by MRI or the like, image disturbance occurs, and diagnosis based on a captured image is difficult. On the other hand, with the rod disclosed in Patent Literature 1, although there is no such problem, it is found that it is difficult to impart desired rigidity because the fiber density is low, and there is difficulty in strength and durability.

One object of the present disclosure is to provide a fixture rod that reduces damage at the time of fixing with a screw, has high rigidity, and has high durability against a deformation load. Other objects of the present disclosure will become apparent by reference to the entire specification.

A fixture rod according to one embodiment of the present disclosure is configured to comprise a core member and a reinforcing fiber layer provided on the core member.

The fixture rod according to one embodiment of the present disclosure is configured to comprise a covering layer provided on the reinforcing fiber layer.

In the fixture rod according to one embodiment of the present disclosure, the core member is formed by a resin containing a fiber.

In the fixture rod according to one embodiment of the present disclosure, the fiber is any of carbon, glass, aramid, boron, or SiC, and the resin is any of epoxy, phenol, unsaturated polyester, PA, PC, PPSU, POM, PP, PE, ABS, PS, PAEK, or PEEK.

In the fixture rod according to one embodiment of the present disclosure, the reinforcing fiber layer is a fiber-reinforced resin, carbon, glass, boron, SiC, or aramid is used as a fiber, and epoxy, phenol, unsaturated polyester, PA, PC, PPSU, POM, PP, PE, ABS, PS, PAEK, or PEEK is used as a resin.

In the fixture rod according to one embodiment of the present disclosure, it is configured such that a fiber of the reinforcing fiber layer is a long fiber.

In the fixture rod according to one embodiment of the present disclosure, it is configured such that a fiber content of the reinforcing fiber layer is 60 weight % or more.

In the fixture rod according to one embodiment of the present disclosure, the reinforcing fiber layer comprises a plurality of reinforcing fiber layers, and at least one of the reinforcing fiber layers is an oblique fiber layer in which a fiber direction is inclined with respect to an axial length direction.

In the fixture rod according to one embodiment of the present disclosure, the oblique fiber layer has a fiber angle in a range of 5° to 85° or −5° to −85°.

In the fixture rod according to one embodiment of the present disclosure, fiber directions of the reinforcing fiber layers are aligned, and thicknesses of the layers are in a range of 0.02 mm to 0.25 mm.

In the fixture rod according to one embodiment of the present disclosure, when the reinforcing fiber layer comprises a plurality of reinforcing fiber layers, a bending elastic modulus of a fiber used in at least one or more reinforcing fiber layers of the plurality of reinforcing fiber layers is larger than a bending elastic modulus of the core member.

According to each of the above embodiments of the present disclosure, it is possible to provide a fixture rod that reduces damage at the time of fixing with a screw, has high rigidity, and has high durability against a deformation load.

DETAILED DESCRIPTION

Figure 1:
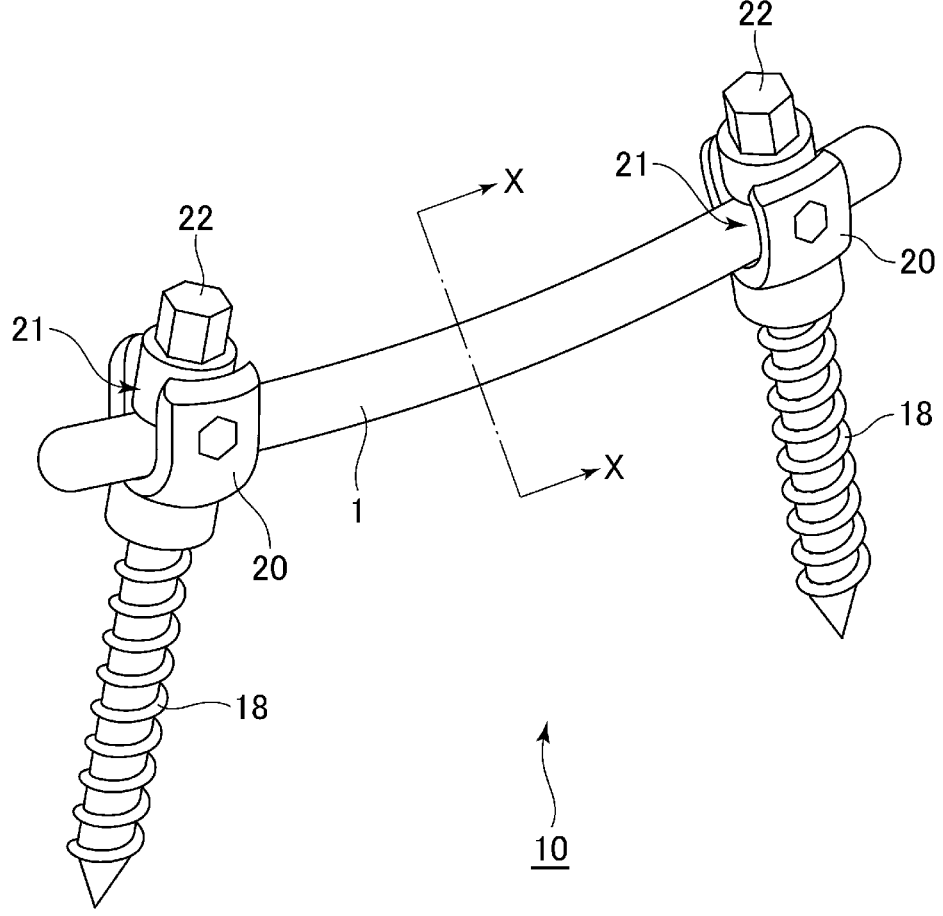
FIG. 1 is a view illustrating a spinal fixture 10 comprising a fixture rod according to one embodiment of the present disclosure.

Hereinafter, an embodiment of a fixture rod according to the present disclosure will be specifically described with reference to the accompanying drawings. Components common in the plurality of drawings are denoted by the same reference numerals throughout the plurality of drawings. Note that the drawings are not necessarily drawn to scale for convenience of description.

FIG. 1 is a view illustrating a spinal fixture 10 comprising a fixture rod 1 according to one embodiment of the present disclosure. As illustrated in the drawing, the spinal fixture 10 comprises a plurality of screw members 18 (two screw members 18 in the example illustrated in the drawing) to be fixed to the bone of the spine, a plurality of rod fixing members 20 (two rod fixing members 20 in the example illustrated in the drawing) attached to the screw members 18 and each comprising a recess 21 for receiving the fixture rod and a pressing member 22, and the fixture rod 1 inserted into the recess 21 of the plurality of rod fixing members 20 and fixed by the pressing member 22.

Figure 2:
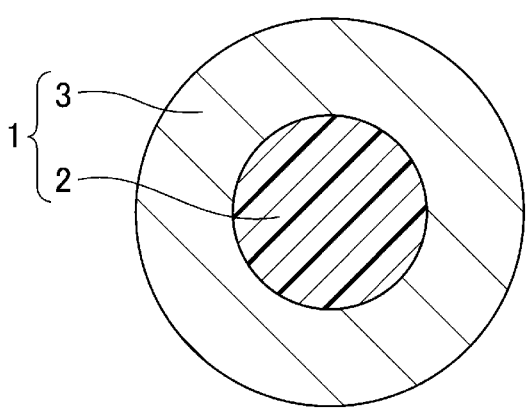
FIG. 2 is a view schematically illustrating a cross section of the fixture rod according to one embodiment of the present disclosure taken along a plane perpendicular to a central axis thereof.

Next, the fixture rod 1 according to one embodiment of the present disclosure used for the spinal fixture 10 will be described with reference to FIG. 2. FIG. 2 illustrates the fixture rod 1 illustrated in FIG. 1 in the X-X section as illustrated in FIG. 1. As illustrated in the drawing, it is configured such that the fixture rod 1 according to one embodiment of the present disclosure comprises a core member 2 and a reinforcing fiber layer 3 provided on the core member 2.

With the fixture rod 1 according to one embodiment of the present disclosure, it is possible to provide a fixture rod that reduces damage at the time of fixing with the screw, has high rigidity, and has high durability against a deformation load. More specifically, since a solid double structure is employed and a material having a large average bending elastic modulus is used for the outer layer as described later, it is possible to provide the fixture rod having excellent bending rigidity and crushing strength of the entire rod. Here, the average bending elastic modulus refers to a value calculated by dividing the bending rigidity of the entire corresponding portion by a second moment of the corresponding portion.

Further, it is configured such that the fixture rod 1 according to one embodiment of the present disclosure comprises a covering layer provided on the reinforcing fiber layer 3. The covering layer can be formed by, for example, epoxy, phenol, unsaturated polyester, PA, PC, PPSU, POM, PP, PE, ABS, PS, PAEK, or PEEK, but is not limited thereto.

In the fixture rod 1 according to one embodiment of the present disclosure, the core member 2 is formed by a resin containing a fiber. Further, in the fixture rod 1 according to one embodiment of the present disclosure, it is configured such that the fiber is any of carbon, glass, aramid, boron, or SiC, and the resin is a thermosetting resin (for example, epoxy, phenol, unsaturated polyester, and the like) or a thermoplastic resin (for example, PA, PC, PPSU, POM, PP, PE, ABS, PS, PAEK, PEEK, or the like). With this configuration, it is possible to increase the bending rigidity and the strength of the core member.

In the fixture rod 1 according to one embodiment of the present disclosure, the reinforcing fiber layer 3 is a fiber-reinforced resin, carbon, glass, boron, SiC, or aramid is used as a fiber, and a thermosetting resin (for example, epoxy, phenol, unsaturated polyester, and the like) or a thermoplastic resin (for example, PA, PC, PPSU, POM, PP, PE, ABS, PS, PAEK, PEEK, or the like) is used as a resin. With this configuration, it is possible to increase the bending rigidity and the strength of the reinforcing fiber layer.

In the fixture rod 1 according to one embodiment of the present disclosure, it is configured such that a fiber of the reinforcing fiber layer 3 is a long fiber. Since the fibers of the reinforcing fiber layer 3 are long fibers, it is possible to further increase the bending rigidity and the strength.

Further, in the fixture rod 1 according to one embodiment of the present disclosure, it is configured such that a fiber content of the reinforcing fiber layer 3 is 60 weight % or more. With this configuration, it is possible to form the fixture rod 1 having high rigidity and excellent durability due to the fiber layer in which the long fibers are focused in high density.

Figure 3:
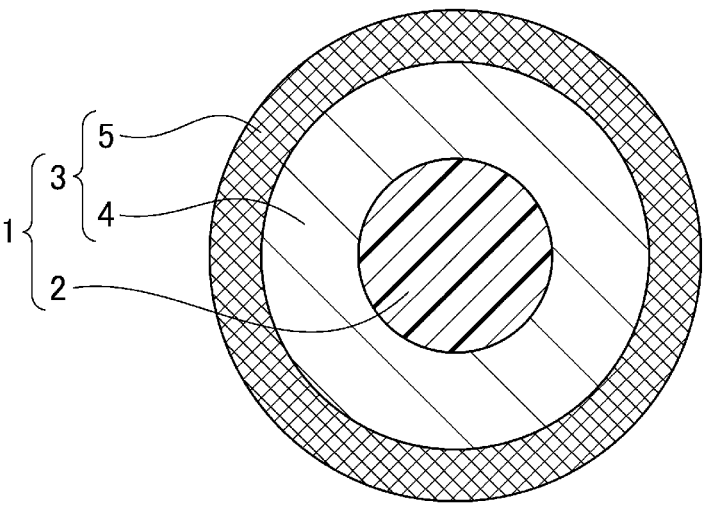
FIG. 3 is a view schematically illustrating a cross section of the fixture rod according to one embodiment of the present disclosure taken along a plane perpendicular to a central axis thereof.

Next, the fixture rod 1 according to one embodiment of the present disclosure will be described with reference to FIG. 3. As illustrated in the drawing, it is configured such that the fixture rod 1 according to one embodiment of the present disclosure comprises a core member 2 and a reinforcing fiber layer 3 provided on the core member 2, and the reinforcing fiber layer 3 comprises an axial long fiber layer 4 in which a fiber direction is oriented in an axial length direction (front-back direction of a paper surface), and an oblique fiber layer 5 in which the fiber direction is inclined from the axial length direction. The axial long fiber layer 4 has advantages in terms of bending rigidity and bending strength, and the oblique fiber layer 5 has advantages in terms of torsional rigidity and torsional strength, so that it is possible to provide a fixture rod that reduces breakage at the time of fixing with the screw, has high rigidity, and has high durability against a deformation load by the core member 2 and the reinforcing fiber layer 3.

Further, in the fixture rod 1 according to one embodiment of the present disclosure, it can be configured such that the reinforcing fiber layer 3 comprises a plurality of reinforcing fiber layers, and at least one of the reinforcing fiber layers is an oblique fiber layer in which a fiber direction is inclined with respect to an axial length direction. With this configuration, since the oblique fiber layer 5 has advantages in terms of torsional rigidity and torsional strength, it is possible to provide a fixture rod that reduces damage at the time of fixing with the screw and has high rigidity and high durability against a deformation load by the core member 2 and the reinforcing fiber layer 3.

In the fixture rod 1 according to one embodiment of the present disclosure, the oblique fiber layer has a fiber angle in a range of 5° to 85° or −5° to −85°. Considering the torsional rigidity and the torsional strength, a most effective fiber angle of the oblique fiber layer is about ±45°. This is because the shear modulus at ±45° is maximized and the torsional rigidity is also maximized.

Further, in the fixture rod 1 according to one embodiment of the present disclosure, fiber directions of the reinforcing fiber layers are aligned, and thicknesses of the layers are, for example, in a range of 0.02 mm to 0.25 mm. With this configuration, the density of the resin is made uniform, and the variation in strength depending on the portion can be reduced. Further, in the fixture rod according to one embodiment of the present disclosure, when the reinforcing fiber layer comprises a plurality of reinforcing fiber layers, a bending elastic modulus of a fiber used in at least one or more reinforcing fiber layers of the plurality of reinforcing fiber layers is larger than a bending elastic modulus of the core member. With this configuration, by combining the reinforcing fiber layer with the core member while imparting certain elasticity to the reinforcing fiber layer, it is possible to maintain high bending rigidity and crushing strength of the entire rod.

Next, the fixture rod 1 according to one embodiment of the present disclosure will be described with reference to FIGS. 4 and 5. As illustrated in the drawing, it is configured such that the fixture rod 1 according to one embodiment of the present disclosure comprises a core member 2 and a reinforcing fiber layer 3 provided on the core member 2. The core member 2 is formed by PEEK/CF (short fiber), and has an outer shape of about 3.0 mm.

As illustrated in the drawing, the reinforcing fiber layer 3 is formed by a first stacked layer 6, a second stacked layer 7, and a third stacked layer 8. It is configured such that the first stacked layer 6 is formed by bonding a glass scrim to a UD, the UD has a fiber elastic modulus of 30 t, a resin content (RC) of 24%, and a thickness of about 0.103 mm, and the scrim has a fiber elastic modulus of 7 t, a resin content (RC) of 28%, and a thickness of 0.012 mm.

In addition, it is configured such that the second stacked layer 7 is formed by bonding two oblique layers together, and the oblique layer has a fiber elastic modulus of 30 t, a resin content (RC) of 30%, a thickness of about 0.051 mm, and an oblique angle of +45° or −45°.

It is configured such that the third stacked layer 8 is formed by bonding a glass scrim to a UD, the UD has a fiber elastic modulus of 30 t, a resin content (RC) of 24%, and a thickness of about 0.103 mm, and the scrim has a fiber elastic modulus of 7 t, a resin content (RC) of 28%, and a thickness of 0.012 mm.

Figure 4:
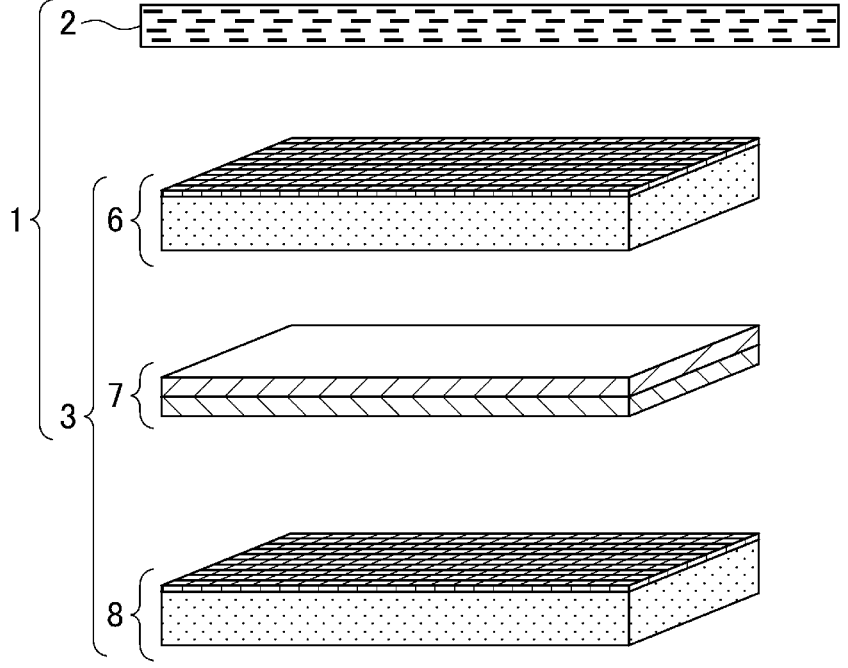
FIG. 4 is a view illustrating each layer of the fixture rod according to one embodiment of the present disclosure.
Figure 5:
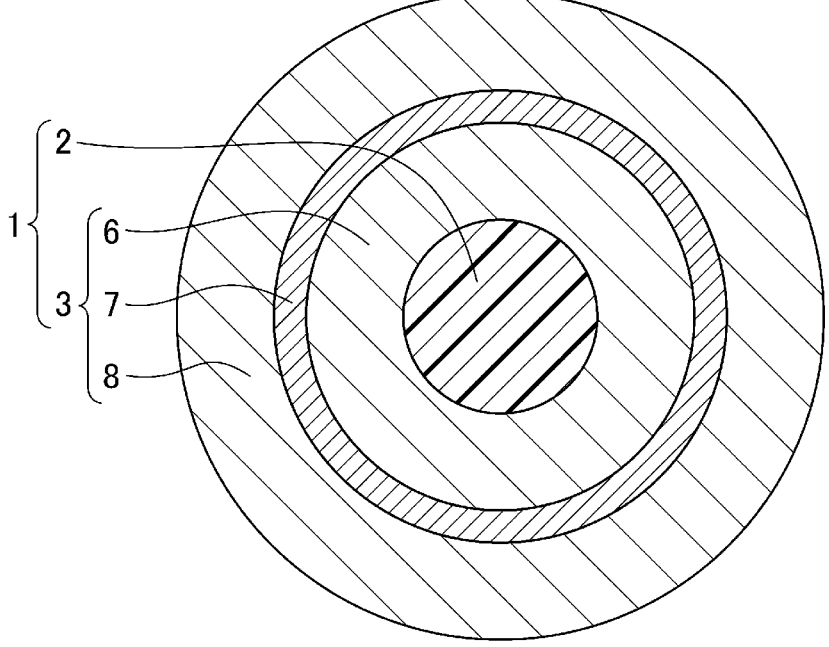
FIG. 5 is a view schematically illustrating a cross section of the fixture rod according to one embodiment of the present disclosure taken along a plane perpendicular to a central axis thereof.

FIG. 5 illustrates the fixture rod 1 according to one embodiment of the present disclosure in which each layer as illustrated in FIG. 4 is formed, as viewed in the X-X cross-section in FIG. 1. As illustrated in the drawing, the fixture rod 1 according to one embodiment of the present disclosure comprises a core member 2 and a reinforcing fiber layer 3 provided on the core member 2, and the reinforcing fiber layer 3 is formed by the first stacked layer 6, the second stacked layer 7, and the third stacked layer 8 described above.

With the fixture rod 1 according to one embodiment of the present disclosure, it is possible to provide a fixture rod that reduces damage at the time of fixing with the screw, has high rigidity, and has high durability against a deformation load. More specifically, since a solid double structure is employed and a material having a large average bending elastic modulus is used for the outer layer as described later, it is possible to provide the fixture rod having excellent bending rigidity and crushing strength of the entire rod. Here, the average bending elastic modulus refers to a value calculated by dividing the bending rigidity of the entire corresponding portion by the second moment of the corresponding portion.

Next, a method for manufacturing the fixture rod 1 according to one embodiment of the present disclosure will be described. First, as step 1, the prepreg is cut (cutting of the prepreg). Then, as step 2, a core material (for example, carbon solid (long fiber)) is prepared. As step 3, since the core material has no stiffness, a V-groove rail illustrated in FIG. 6(*a*) is used, and a temporary fixing resin is applied to perform temporary fixing (tentative fixing). In step 4, wrapping with the prepreg is performed.

Figure 6:
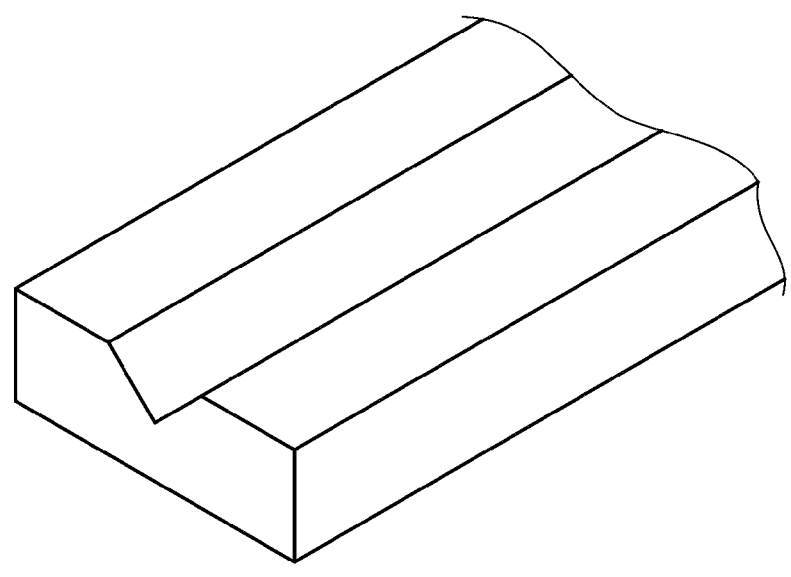
FIGS. 6(a) and 6(b) are views illustrating a member used for manufacturing the fixture rod according to one embodiment of the present disclosure.
Figure 6:
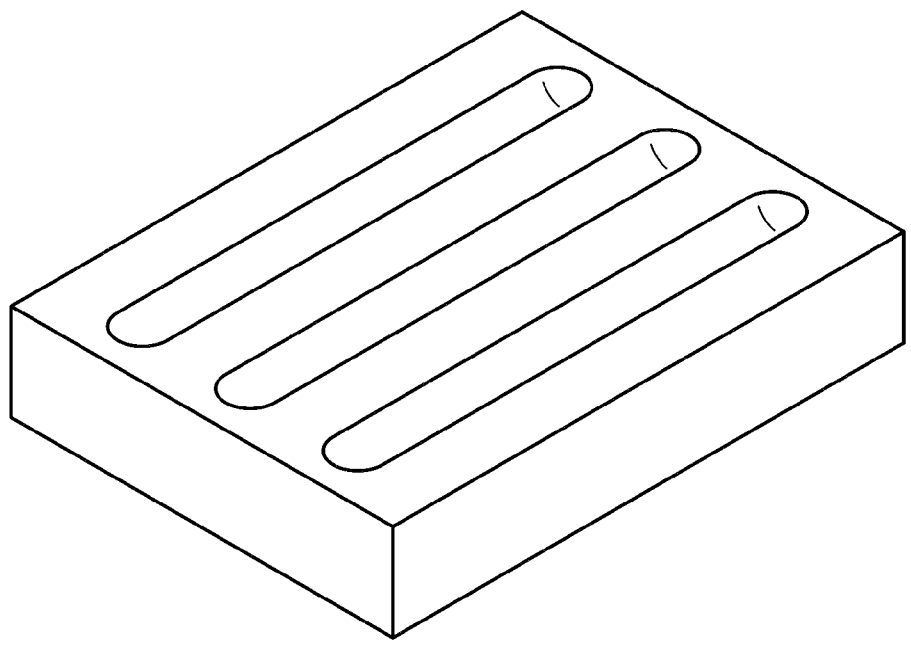

Next, in step 5, curing is performed using a grooved straightening die illustrated in FIG. 6(*b*). The reason for using the straightening die is that it may be slightly bent at the time of winding in step 4 described above, and thus needs to be straightened. Then, cutting is performed in step 6, a tape is removed in step 7, and finally, centerless is performed for outer diameter adjustment in step 8.

With the fixture rod 1 formed in this manner according to one embodiment of the present disclosure, it is possible to provide a fixture rod that reduces damage at the time of fixing with a screw, has high rigidity, and has high durability against a deformation load. More specifically, since a solid double structure is employed and a material having a large average bending elastic modulus is used for the outer layer as described later, it is possible to provide the fixture rod having excellent bending rigidity and crushing strength of the entire rod. Here, the average bending elastic modulus refers to a value calculated by dividing the bending rigidity of the entire corresponding portion by the second moment of the corresponding portion.

The dimensions, materials, and arrangement of components described herein are not limited to those explicitly described in the embodiments, and each component may be modified to have any dimensions, material, and arrangement that may fall within the scope of the present disclosure. In addition, components not explicitly described herein can be added to the described embodiments, or some of the components described in each embodiment can be omitted.

REFERENCE SIGNS LIST

1 Fixture rod
2 Core member
3 Reinforcing fiber layer
4 Axial long fiber layer
5 Oblique fiber layer
6 First stacked layer
7 Second stacked layer
8 Third stacked layer
10 Spinal fixture
18 Screw member
20 Rod fixing member
21 Recess
22 Pressing member

The invention claimed is:

1. A fixture rod, comprising:
a core member; and a plurality of reinforcing fiber layers provided on the core member,
wherein (i) at least one of the plurality of reinforcing fiber layers is an oblique fiber layer in which a fiber direction is inclined with respect to an axial length direction of the fixture rod, and the oblique fiber layer has a fiber angle in a range of 5° to 85° or −5° to 85°, (ii) another one of the plurality of reinforcing fiber layers includes an axial long fiber layer in which a fiber direction is oriented in the axial length direction of the fixture rod, and (iii) the oblique fiber layer surrounds the axial long fiber layer.

2. The fixture rod according to claim 1, wherein the core member is formed by a resin containing a fiber.

3. The fixture rod according to claim 2, wherein the fiber is any of carbon, glass, aramid, boron, or SiC, and the resin is any of epoxy, phenol, unsaturated polyester, PA, PC, PPSU, POM, PP, PE, ABS, PS, PAEK, or PEEK.

4. The fixture rod according to claim 1, wherein the plurality of reinforcing fiber layers are fiber-reinforced resins, and wherein carbon, glass, boron, SiC, or aramid is used as a fiber in the fiber-reinforced resins, and wherein epoxy, phenol, unsaturated polyester, PA, PC, PPSU, POM, PP, PE, ABS, PS, PAEK, or PEEK is used as a resin in the fiber-reinforced resins.

5. The fixture rod according to claim 1, wherein a fiber content of the plurality of reinforcing fiber layers is 60 weight % or more.

6. The fixture rod according to claim 1, wherein fiber directions of the plurality of reinforcing fiber layers are aligned, and thicknesses of the layers are in a range of 0.02 mm to 0.25 mm.

7. The fixture rod according to claim 1, wherein a bending elastic modulus of a fiber used in at least one or more of the plurality of reinforcing fiber layers is larger than a bending elastic modulus of the core member.

8. The fixture rod according to claim 1, wherein the core member is formed by a resin containing short fibers.

* * * * *